United States Patent [19]
Willmitzer et al.

[11] Patent Number: 6,057,493
[45] Date of Patent: May 2, 2000

[54] PLASMIDS, PLANTS AND PLANT CELLS EXPRESSING ANTI-SENSE PATATIN AND ANTI-SENSE ADP-GLUCOSE PYROPHOSPHORYLASE SEQUENCES

[75] Inventors: Lothar Willmitzer; Uwe Sonnewald; Rainer Höfgen; Jens Kossmann; Bernd Müller, all of Berlin, Germany

[73] Assignee: Hoechst Schering AgrEvo GmbH, Berlin, Germany

[21] Appl. No.: 08/177,719

[22] Filed: Jan. 5, 1994

Related U.S. Application Data

[63] Continuation of application No. 07/686,695, Apr. 17, 1991, abandoned.

[30] Foreign Application Priority Data

Apr. 20, 1990 [DE] Germany ............................ 40 13 144

[51] Int. Cl.$^7$ ............................ A01H 5/00; C12N 15/29; C12N 15/54; C12N 15/82; C12N 5/04
[52] U.S. Cl. ........................ 800/284; 800/286; 800/287; 800/298; 800/317.2; 435/69.1; 435/100; 435/101; 435/320.1; 435/417; 435/419; 435/468; 435/194
[58] Field of Search .................. 435/69.1, 70.1, 435/172.3, 240.4, 320.1, 417, 419, 100, 101, 468, 194; 800/205, DIG. 42, 284, 286, 287, 298, 317.2

[56] References Cited

U.S. PATENT DOCUMENTS

| | | | |
|---|---|---|---|
| 4,630,393 | 12/1986 | Bonucci ........................................ | 47/58 |
| 5,792,920 | 8/1998 | Bridges et al. ......................... | 800/205 |

FOREIGN PATENT DOCUMENTS

| | | | |
|---|---|---|---|
| 0305275 | 1/1989 | European Pat. Off. ........ | C12N 15/00 |
| 0368506 | 5/1990 | European Pat. Off. ........ | C12N 15/54 |
| 0449376 | 2/1991 | European Pat. Off. .......... | C12N 9/28 |
| 8908145 | 9/1989 | WIPO ............................. | C12N 15/00 |
| 9012084 | 10/1990 | WIPO ............................. | C12N 5/00 |
| 9012876 | 11/1990 | WIPO ............................. | C12N 15/56 |
| 9309237 | 5/1993 | WIPO ............................. | C12N 15/82 |

OTHER PUBLICATIONS

Embo Journal, vol. 8, No. 1, Jan. 1989, pp. 23–29, IRL Press; M. Rochasosa et al.: "Both developmental and metabolic signals activate the promoter of a class I patatin gene", p. 25, left-hand column.

The Plant Cell, vol. 2, No. 1, Jan. 1990, pp. 7–18, American Society of Plant Physiologists; L.M. Lagrimini et al.: "Peroxidase-induced wilting in transgenic tobacco plants".

Plant Mol. Biol., vol. 14, No. 3, Mar. 1990, pp. 369–379, Kluwer Academic Publishers, BE; C.J.S. Smith et al.: "Inheritance and effect on ripening of antisense polygalacturonase genes in transgenic tomatoes".

The Plant Cell, vol. 3, No. 3, Mar. 1991, pp. 213–218, American Society of Plant Physiologists; M.F. Dilworth: "Molecular biology comes home", p. 216, right-hand column, last paragraph–p. 217, left-hand column, paragraph 1.

Journal of Cellular Biochemistry, Supplement 14E, UCLA Symposia on Molecular & Cellular Biology, Abstracts, 19th Annual Meetings, Mar. 31–Apr. 22, 1990, p. 271, Abstract R 028, Wiley–Liss; R.G.F. Visser et al.: Manipulation of Starch in potatoes by new mutants and antisense RNA.

Chemical Abstracts, vol. 64, 1966, Abstract No. 10103b–c, Columbus, Ohio, US; C.Y. Tsai et al.: "Starch–deficient maize mutant lacking adenosine diphosphate glucose pyrophosphorylase activity", & Science 151 (3708), 341–3 (1966).

Plant Physiol., vol. 92, Apr. 1990, pp. 881–885; J. Preiss et al.: Molecular characterization of the Brittle–2 gene effect on maize endospern ADP glucose pyrophosphorylase subunits.

The Journal of Biological Chemistry, vol. 264, No. 21, Jul. 25, 1989, pp. 12238–12242, The American Society for Biochemistry and Molecular Biology, Inc., US; J.M. Anderson et al.: The encoded primary sequence of a rice seed ADF–glucose pyrophosphorylase subunit and its homology to the bacterial enzyme.

Plant Physiol., vol. 57, 1976, pp. 63–68; J.R. Sowokinos: "Pyrophosphorylases in solanum tuberosum".

Journal of Cellular Biochemistry, supplement 14E, UCLA Symposia on Molecular & Cellular Biology, Abstract, 19th Annual Meetings, Mar. 31–Apr. 22, 1990, p. 270, Abstracts No. R 027, Wiley–Liss; L.C. Hannah et al.: "Molecular and genetic aspects of genes important in starch biosynthesis".

Sowokinos et al. 1985, Plant Physiol. 78(3):489–494.

Anderson et al. 1990, pp. 159–180 In: Molec. Cell. Biol. Potato, Vayda et al., eds., C.A.B. Int.: Wallingford, UK.

Yang et al. 1989, Plant Science 64(1):99–11.

Mueller–Roeber et al. 1990, Mol. Cren. Aenet. 224(1):136–146.

Sheehy et al. 1988, Proc. Natl. Acad. Sci. USA 85(23):8805–8809.

Khursheed et al. 1988, J. Biol. Chem. 263(35):18953–18960.

Neuhaus et al. 1990, Planta 182:445–454.

*Primary Examiner*—David T. Fox
*Attorney, Agent, or Firm*—Frommer Lawrence & Haug LLP

[57] ABSTRACT

Plasmids containing DNA sequences which when inserted into the genome of a plant modify the carbohydrate or protein concentration and the carbohydrate or protein composition, and plant cells and plants that contain these plasmids.

DNA sequences located in plasmids reduce ADP-glucose-pyrophosphorylase activity in the plant and thereby the starch concentration, while at the same time increase the mono- and oligosaccharide concentration. Other DNA sequences in plasmids reduce or increase the protein concentration. Plants that contain these plasmids are suitable inter alia for the extraction of sugar or as protein-enriched food or fodder.

26 Claims, 5 Drawing Sheets

PLASMIDS, PLANTS AND PLANT CELLS EXPRESSING ANTI-SENSE PATATIN AND ANTI-SENSE ADP-GLUCOSE PYROPHOSPHORYLASE SEQUENCES

This is a file wrapper continuation application of application Ser. No. 07/686,695 filed on Apr. 17, 1991, now abandoned.

FIELD OF THE INVENTION

The present invention relates to plasmids containing DNA sequences, which when inserted into the genome of a plant material bring about changes in its carbohydrate and protein concentration and in the carbohydrate and protein composition of plants regenerated from this material. The invention relates also to plant cells and plants that contain these plasmids.

Owing to the continuously increasing need for food and raw materials as the result of a constantly growing world population, one of the tasks of biotechnological research is to seek to modify the contents and the yield of productive plants. This task involves modifying the metabolism of the plants.

Of special interest is the possibility of using plant products as renewable sources of raw materials for, for example, the chemical industry. This possibility is of especially great significance for two reasons. Firstly, oil and coal deposits were previously the main sources of raw materials used by the petrochemical industry. Those stocks are not endless, however, and it is foreseeable that alternative, renewable sources of raw materials, will be needed in the future. Secondly, the current situation in agriculture is such that there is an excess of the traditional agricultural products aimed at the food sector in Europe and North America, leading to obvious financial and political problems in agriculture. Alternative products for which there is a great need in terms of quantity could represent a solution to that problem.

Raw materials that are renewable can be divided in principle into the categories of fats and oils, proteins, and carbohydrate compounds such as mono-, oligo- and polysaccharides. In the case of the polysaccharides, starch and cellulose are by far the most important examples. Within the European Community (EC), the total starch production for the year 1987/1988 was divided among the plants; maize (60%), wheat (19%) and potatoes (21%). In the case of the oligosaccharides, the disaccharide sucrose is by far the most important substance in terms of quantity. Within the EC, the sugar beet is by far the most important source used in the production and extraction of sucrose.

In order to further expand the industrial exploitation of mono- and oligosaccharides as raw materials and in view of in the high degree of ecological and economical risk inherent in the cultivation of monocultures having a low rate of crop rotation, such as, for example, sugar beets, it is desirable additionally to use plants other than sugar beet in the production of oligosaccharides.

When seeds or tubers are used as the raw material for sugar production, the large amount of liquid involved is a considerable hindrance. In the case of potatoes, the liquid content makes up approximately 80% of the fresh weight of the tuber.

In addition, a large proportion of this liquid contains reduced nitrogen which leads to ecological problems during processing. When using seeds or tubers for the production of sugar, it would therefore be advantageous to reduce the protein content of the seeds or tubers.

On the other hand, an increase in the concentration of protein in seeds and tubers of a plant would be desirable if plant products of improved quality were required, such as, for example, protein-enriched food or cattle fodder.

The biochemical pathways involved in starch synthesis in higher plants are known. Likewise, some of the main proteins of the potato tuber have been well researched biochemically, for example, patatin, the main storage protein of the potato tuber is a glycoprotein having a molecular weight of 40 kDa. (The genomic patatin clone is described by M. Rocha-Sosa et al, loc. cit.) New biotechnological processes for the genetic modification of dicotyledonous and monocotyledonous plants by means of the transfer and stable incorporation of individual isolated genes or groups of genes are known (Gasser and Fraley, Science 244, 1293–1299). Possible means of specific expression, primarily in the tuber, of foreign genes inserted into the potato by means of genetic engineering processes are also known (Rocha-Sosa et al., (1989), EMBO J., 8, 23–29; and EP 375 092).

SUMMARY OF THE INVENTION

An object of the present invention is to provide plasmids containing DNA sequences, which when inserted into the genome of a plant bring about changes in its carbohydrate and protein concentration and in the carbohydrate and protein composition plants regenerated from this material. A further problem of the present invention is to provide plant cells and plants that contain these DNA sequences located in the plasmids.

The present invention provides a plasmid that comprises a DNA sequence that leads, when present in a plant cell, to (a) an increase or a reduction in protein concentration or (b) both a reduction in the concentration of starch and an increase in the concentration of at least one saccharide selected from monosaccharides and oligosaccharides.

The present invention provides a plasmid that comprises a DNA sequence coding for patatin protein, and also provides a plant or a plant cell comprising a DNA sequence that codes for patatin protein; for example, the DNA sequence may be in the form of a plasmid according to the present invention.

The present invention also provides a plasmid that comprises a DNA sequence that codes for the patatin protein, the DNA sequence being present in inverted orientation as hereinafter defined.

The present invention further provides a plasmid that comprises a DNA sequence coding for an ADP-glucose pyrophosphorylase protein, the DNA sequence being present in inverted orientation as hereinafter defined. The DNA sequence may code for one or for both of the sub-units of an ADP-glucose pyrophosphorylase. The DNA sequence codes, for example, for isoform I, for isoform II or for both isoforms of the ADP-glucose pyrophosphorylase of potato.

A DNA sequence in the normal (non-inverted) orientation in a plasmid is arranged such that the 3'-end of the DNA sequence, as defined by the open reading frame, is linked to the 5'-end of the plasmid, and the 5'-end of the DNA is linked to the 3'-end of the plasmid. The DNA may then be read correctly, transcribed and translated. The term "inverted orientation" is used herein to denote that a DNA sequence in a plasmid is arranged such that 3'-end of the DNA sequence, as defined by the open reading frame, is linked to the 3'-end of the plasmid, and 5'-end of the DNA is linked to the 5'-end of the plasmid. When such an inverted construction is transcribed in the host plant the resulting mRNA is "antisense" with respect to the normal "sense" mRNA. A DNA sequence in inverted orientation may be regarded as equivalent to the non-coding strand of that DNA sequence.

In a plasmid of the present invention, the DNA sequence is preferably linked to regulatory sequences that are operative in plant systems and that ensure expression of the DNA sequence in a plant, for example, a promoter and a termination signal of viral and/or of plant genes. The promoter is, for example, the promoter of the 35S RNA of cauliflower mosaic virus and the termination signal is, for example, derived from an octopine synthase gene, for example, from the octopine synthase gene of the T-DNA of Ti-plasmid pTiACH5.

In a plasmid of the invention that comprises a DNA sequence in inverted orientation, a promoter and a termination signal, preferably the 3'-end of the DNA sequence is linked to the 3'-end of the promoter and the 5'-end of the DNA is linked to the 5'-end of the termination signal.

Examples of plasmids according to the present invention are plasmids p35S-pat (DSM 5877), p35S-anti-pat (DSM 5878), p35S-anti-ADP-glc1 (DSM 5879), p35S-anti-ADP-glc2 (DSM 5880) and p35S-anti-ADP-glc1+2 (DSM 5881), which plasmids and their construction are described below.

The present invention also provides a plant or a plant cell that comprises a DNA sequence as defined above, and further provides a plant or a plant cell that comprises a plasmid as defined above.

The present invention further provides the use of a plasmid of the present invention or of a plant cell of the present invention in the production of a transgenic plant.

It has been found that in transgenic plants that comprise a DNA sequence that codes for an ADP-glucose pyrophosphorylase protein, the DNA sequence of which is present in inverted orientation, the DNA sequence being, for example, in a plasmid of the present invention, the ADP-glucose phosphorylase activity and the starch concentration is reduced in comparison with that of untransformed plants, and at the same time the mono- and oligosaccharide concentrations are increased, that is to say, the sugar content is increased. A transgenic plant preferably comprises the gene 35S-anti-glc1, 35S-anti-glc2 or 35S-anti-glc1+2 located in plasmids p35S-anti-ADP-glc1 (DSM 5879), p35S-anti-ADP-glc2 (DSM 5880) and p35S-anti-ADP-glc1+2 (DSM 5881), respectively.

Such transgenic plants may be used as a raw material in the extraction of mono- and oligosaccharides, especially sucrose. Such plants are, for example, potato plants, as the resulting transgenic potato tubers are particularly useful as a raw material for the extraction of mono- and oligosaccharides, especially sucrose, which may then be used in the production of other substances.

It has also been found that in transgenic plants that comprise a DNA sequence that codes for patatin protein, the DNA sequence of which is present in inverted orientation, the DNA sequence being, for example, in a plasmid of the present invention, the protein concentration is reduced in comparison with that of untransformed plants. A transgenic plant preferably comprises the gene 35S-anti-pat located in plasmid p35S-anti-pat (DSM 5878).

As the protein concentration and hence the amount of undesirable nitrogen in the processing liquid is reduced, such transgenic plants may be used as a raw material in the production of sucrose. Such plants are, for example, potato plants, as the resulting transgenic potato tubers are particularly useful as a raw material for sucrose production.

It may be particularly advantageous to construct transgenic plants that comprise both a DNA sequence that codes for an ADP-glucose pyrophlosporylase protein and a DNA sequence that codes for a patatin protein, each of the DNA sequences being present in inverted orientation. The resulting plants have a reduced starch content, an increased content of sugars and a reduced level of protein. Such plants, for example, potato plants, and especially potato tubers, are particularly useful as a raw material for sucrose production.

It has further been found that in transgenic plants that comprise a DNA sequence that codes for patatin protein, the DNA sequence being, for example, in a plasmid of the present invention, the protein concentration is increased in comparison with that of untransformed plants. A transgenic plant preferably comprises the gene 35S-pat located in plasmid p35S-pat (DSM 5877). Such transgenic plants, for example, potato plants, especially the tubers thereof, are useful as protein-enriched food and fodder.

A large number of cloning vectors comprising a replication system in E. coli and a marker that permits selection of the transformed cells are available for preparation for the insertion of foreign genes into higher plants. The vectors comprise, for example, pBR322, pUC series, M13mp series, pACYC184, etc.. Accordingly, the sequence can be inserted into the vector at a suitable restriction site. The resulting plasmid is used for transformation into E. coli. The E. coli cells are cultivated in a suitable nutrient medium, then harvested and lysed. The plasmid is recovered. Sequence analysis, restriction analysis, electrophoreses and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema, In: The Binary Plant Vector System Offset-drukkerij Kanters B. V., Alblasserdam, 1985, Chapter V; Fraley et al., Crit. Rev. Plant Sci., 4: 1–46 and An et al., EMBO J. (1985) 4: 277–287.

Once the inserted DNA has been integrated in the genome it is relatively stable there and, as a rule, does not come out again. It normally contains a selection marker that confers on the transformed plant cells resistance to a biocide or an antibiotic, such as kanamycin, G 418, bleomycin, hygromycin or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using Agrobacterium tumefaciens or Agrobacterium rhizogenes as transformation agent, fusion, injection or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al., Mol. Gen. Genet. (1978), 163: 181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. The plants can be grown in the normal manner and crossed with plants that have the same transformed hereditary factors or other hereditary factors. The resulting hybrid individuals have the corresponding phenotypic properties.

Abbreviations
bp, kb=base pairs, kilobases
D, kDa=dalton, kilodalton
DNA=deoxyribonucleic acid, carrier of genetic information
RNA=ribonucleic acid
SDS=sodium dodecyl sulphate
tris=tris(2-aminoethyl)amine
EDTA=ethylenediaminetetraacetic acid The following plasmids were deposited at the Deutsche Sammlung von Mikroorganismen (DSM) in Brunswick, Federal Republic of Germany on 18.04.1990 (deposit number):

| plasmid | p35S-pat | (DSM 5877) |
| plasmid | p35S-anti-pat | (DSM 5878) |
| plasmid | p35S-anti-ADP-glc1 | (DSM 5879) |
| plasmid | p35S-anti-ADP-glc2 | (DSM 5880) |
| plasmid | p35S-anti-ADP-glc1 + 2 | (DSM 5881) |

The gene 35S-pat is cloned into the polylinker of plasmid BIN19. Also shown are the cleavage sites described in Example 1.

Figure 2:
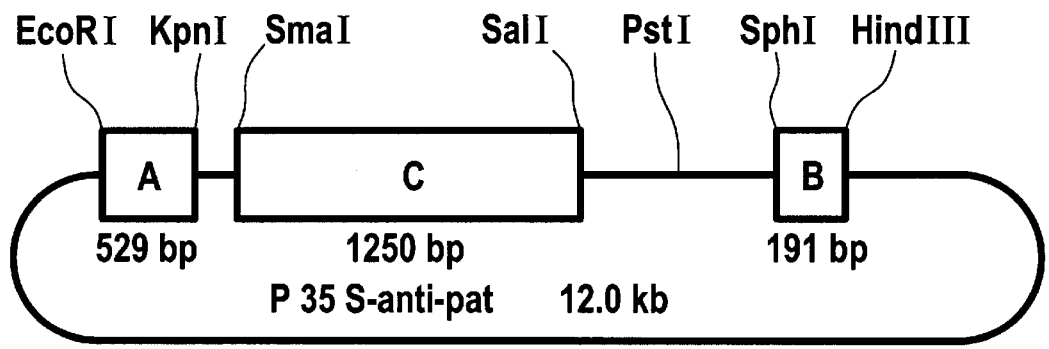

FIG. 2 shows the structure of the 12 kb plasmid p35S-anti-pat. The gene 35S-anti-pat located in the plasmid contains the following fragments:
 A=Fragment A (529 bp) contains the 35S promoter of cauliflower mosaic virus (CaMV). That fragment includes the nucleotides 6909 to 7437 of CaMV.
 B=Fragment B (191 bp) contains the polyadenylation signal of gene 3 of the T-DNA of the Ti-plasmid pTiACH5. That fragment includes the nucleotides 11749–11939.
 C=Fragment C (1250 bp) contains the Sal I/Sma I fragment (see Example 2).

The gene 35S-anti-pat is cloned into the polylinker of plasmid BIN19. Also shown are the cleavage sites described in Example 2.

Figure 3:
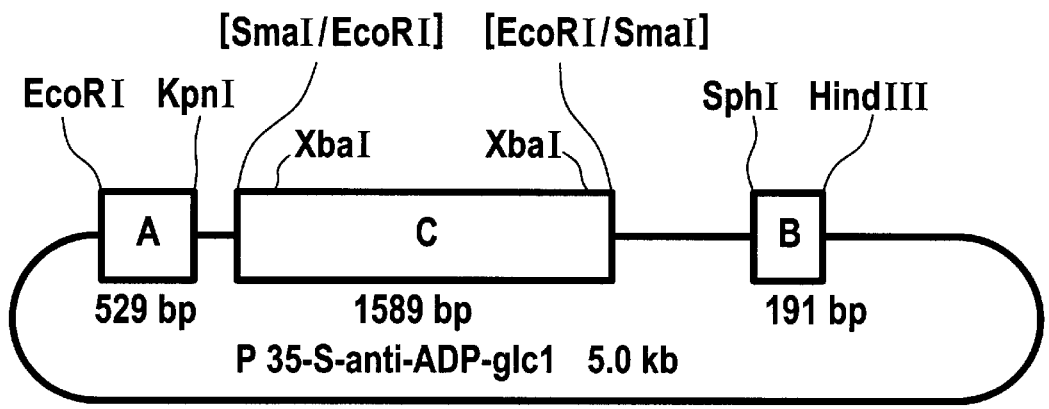

FIG. 3 shows the structure of the 5.0 kb plasmid p35S-anti-ADP-glc1. The gene 35S-anti-ADP-glc1 located in the plasmid contains the following fragments:
 A=Fragment A (529 bp) contains the 35S promoter of cauliflower mosaic virus (CaMV). That fragment includes the nucleotides 6909 to 7437 of CaMV.
 B=Fragment B (191 bp) contains the polyadenylation signal of gene 3 of the T-DNA of the Ti-plasmid pTiACH5. That fragment includes the nucleotides 11749–11939.
 C=Fragment C (1589 bp) contains the Eco RI fragment that codes for isoform I of the two isoforms of the potato ADP-glucose pyrophosphorylase.

The gene 35S-anti-ADP-glc1 is cloned into the polylinker of the plasmid pUC18. Also shown are the cleavage sites described in Example 3.

Figure 4:
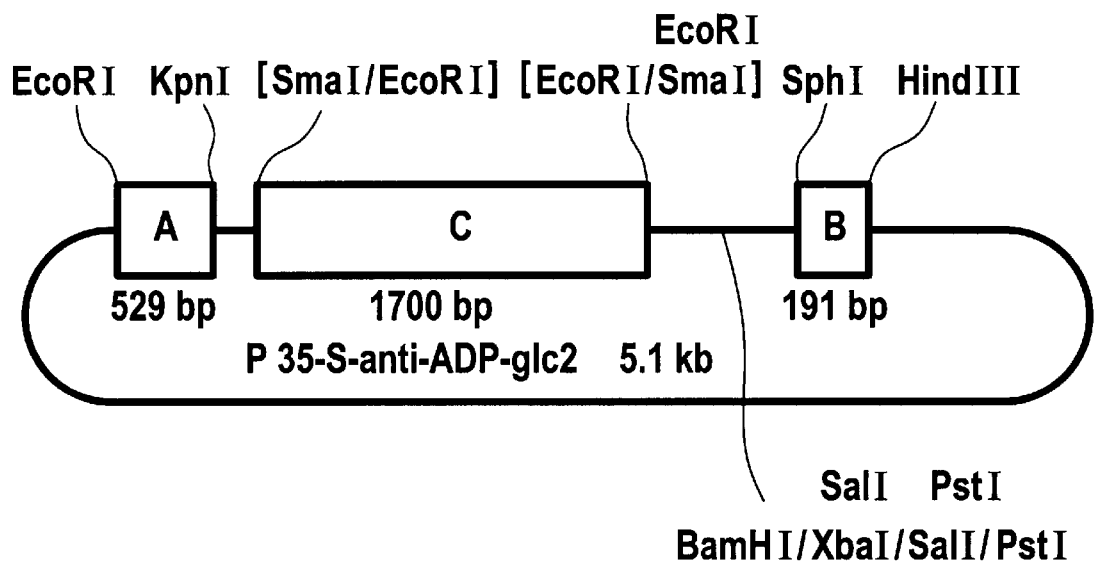

FIG. 4 shows the structure of the 5.1 kb plasmid p35S-anti-ADP-glc2. The gene 35S-anti-ADP-glc2 located in the plasmid contains the following fragments:
 A=Fragment A (529 bp) contains the 35S promoter of cauliflower mosaic virus (CaMV). That fragment includes the nucleotides 6909 to 7437 of CAMV.
 B=Fragment B (191 bp) contains the polyadenylation signal of gene 3 of the T-DNA of the Ti-plasmid pTiACH5. That fragment includes the nucleotides 11749–11939.
 C=Fragment C (1700 bp) contains the Eco RI fragment that codes for isoform II of the two isoforms of the potato ADP-glucose pyrophosphorylase.

The gene 35S-anti-ADP-glc2 is cloned into the polylinker of the plasmid pUC18. Also shown are the cleavage sites described in Example 4.

Figure 5:
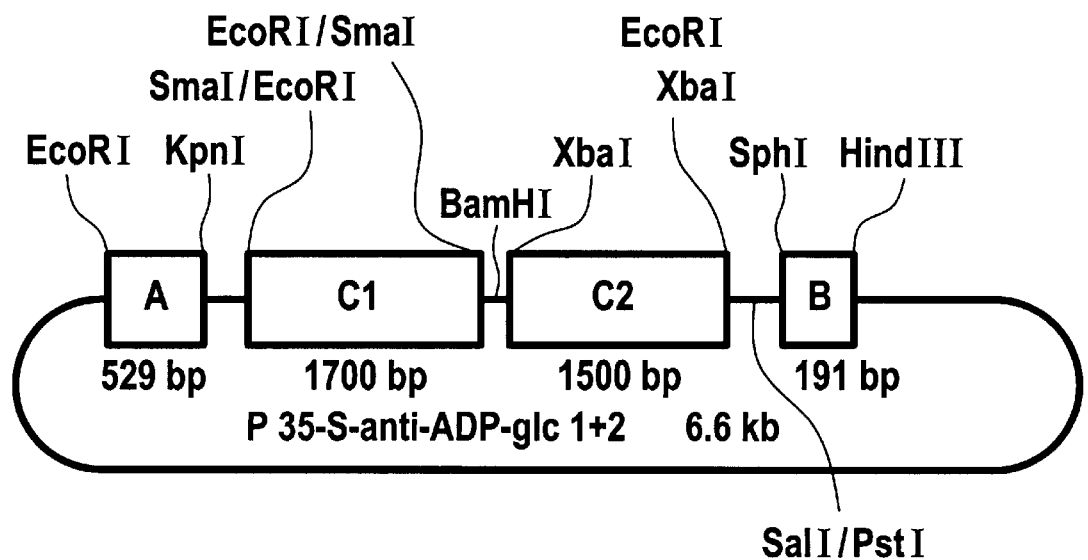

FIG. 5 shows the structure of the 6.6 kb plasmid p35S-anti-ADP-glc1+2. The gene 35S-anti-ADP-glc1+2 located in the plasmid contains the following fragments:
 A=Fragment A (529 bp) contains the 35S promoter of cauliflower mosaic virus (CaMV). That fragment includes the nucleotides 6909 to 7437 of CaMV.
 B=Fragment B (191 bp) contains the polyadenylation signal of gene 3 of the T-DNA of the Ti-plasmid pTiACH5. That fragment includes the nucleotides 11749–11939.
 C1=Fragment C1 (1700 bp) contains the Eco RI fragment that codes for the cDNA of isoform II of the potato ADP-glucose pyrophosphorylase.
 C2 =Fragment C2 (1500 bp) contains the XbaI/Xba I fragment of p35S-anti-ADP-glc1 that codes for the cDNA of isoform I of the potato ADP-glucose pyrophosphorylase.

The gene 35S-anti-ADP-glc1+2 is cloned into the polylinker of the plasmid pUC18. Also shown are the cleavage sites described in Example 5.

Figure 6:
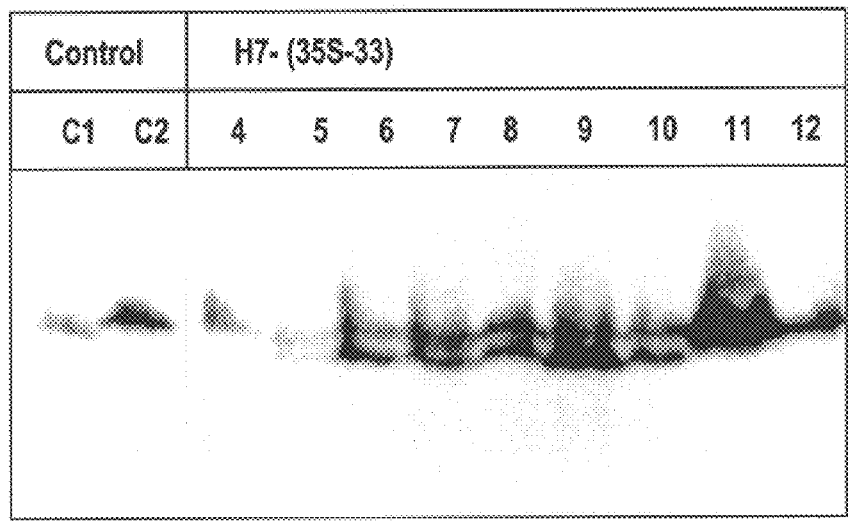

FIG. 6 shows the in situ detection of esterase activity in tuber extracts from independent transformed potato plants of the Désirée variety. Gel region showing the esterase. The black spots of tracks 4–11 show the esterase activity in 8 H7-(35S-33) plants transformed with gene 35S-pat in contrast to the controls C1 and C2 (first and second track), which are controls of untransformed plants. The arrows (→) indicate the range of the esterase activity.

Figure 7:
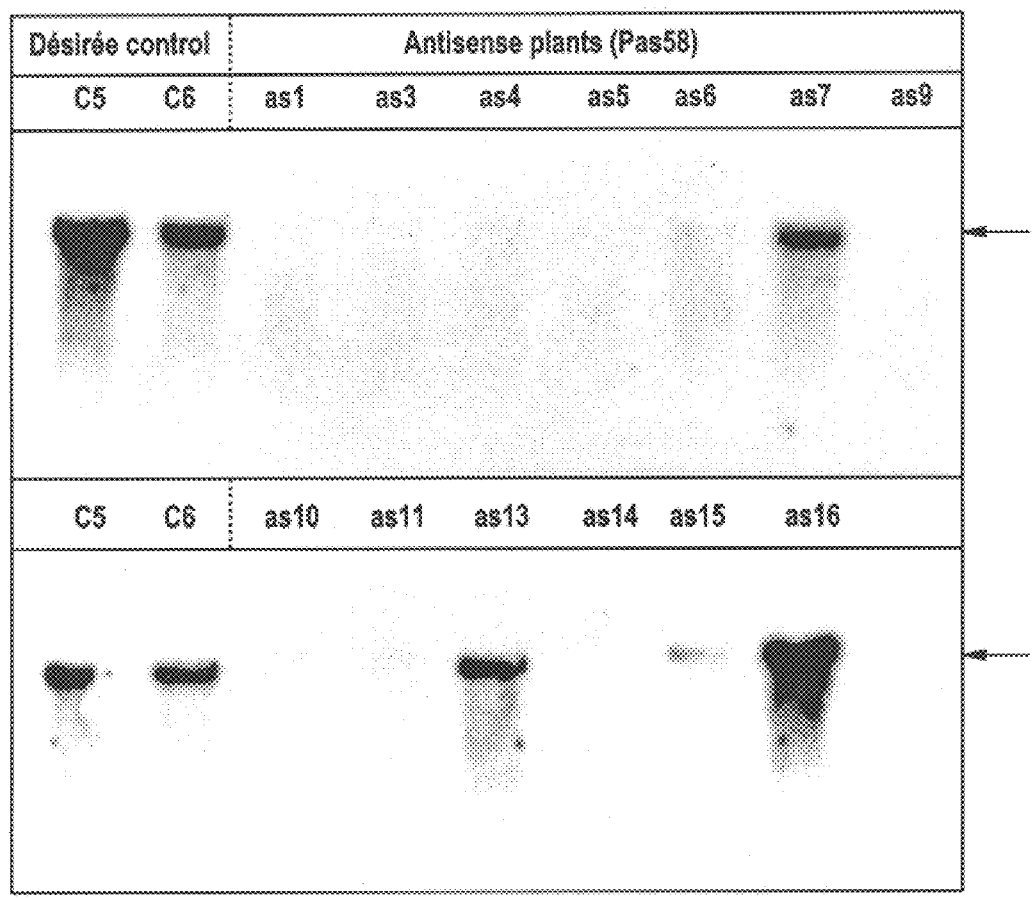

FIG. 7 shows the bands of patatin RNA rendered visible by autoradiography. The bands are marked by an arrow. The intensity of the bands is a measure of the concentration of the particular RNA in question. Positions as1, as3, as4, as5, as6, as7, as9, as10, as11, as13, as14, as15 and as16 contain samples of the RNA isolated from tubers of potato plants transformed with the gene 35S-anti-pat. In samples as1, as3, as4, as5, as6, as9, as10, as11, as14 and as15 a marked reduction in the patatin-sense-RNA concentration in comparison with the controls C5 and C6 of untransformed cells can be seen.

Figure 8:
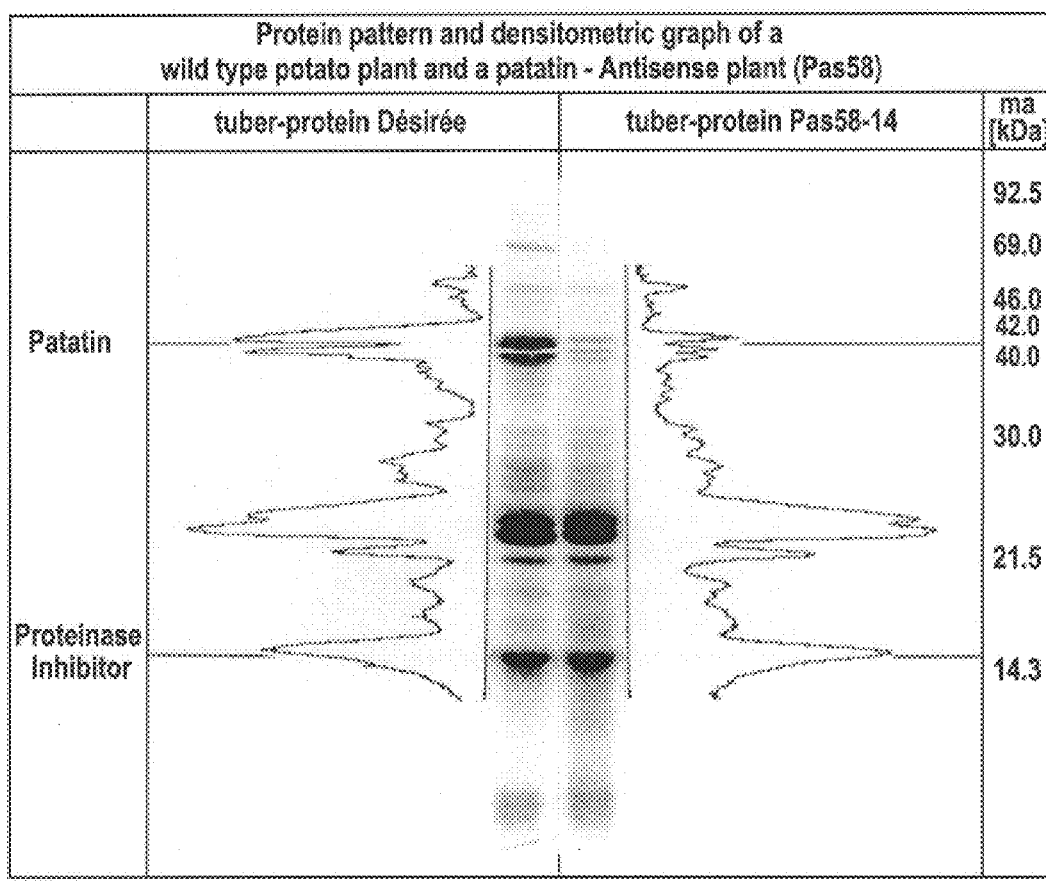

FIG. 8 shows the reduction in the amount of endogenous patatin protein in tubers of a transgenic potato plant transformed with the gene 35S-anti-pat, as well as the corresponding densitometry curves of the proteins.

A=the protein pattern of an untransformed potato tuber of the Désirée variety.

B=the protein pattern of a potato plant transformed with the gene 35S-anti-pat. The intensity of the blackness is a measure of the concentration.

ma=molecular weight

Figure 9:
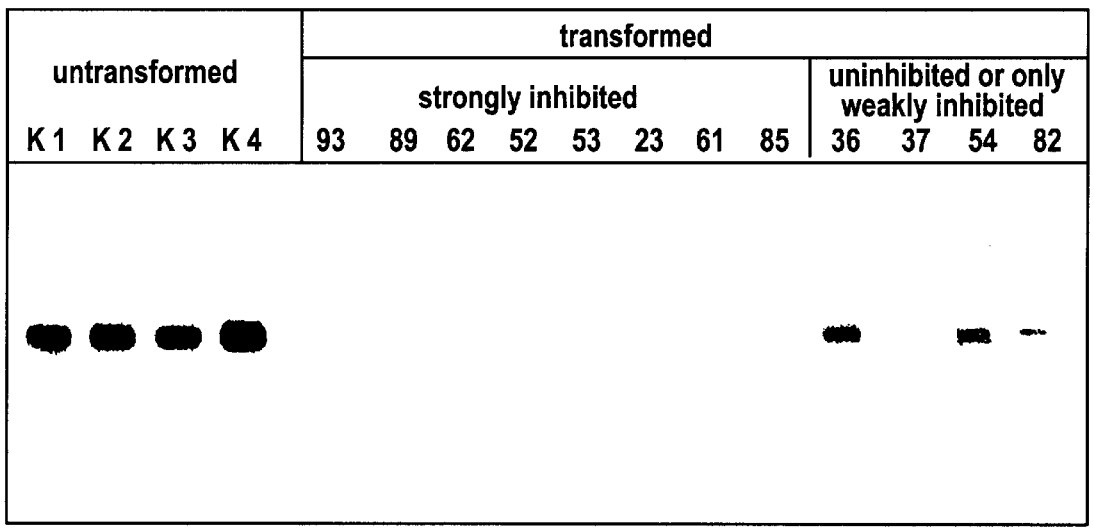

FIG. 9 shows the bands of ADP-glc1-RNA rendered visible by autoradiography. The intensity of the bands is a measure of the concentration of the particular RNA in question. Positions K1-K4 contain RNA from tubers of untransformed plants, positions 93, 89, 62, 52, 53, 23, 61, 85, 36, 37, 54 and 82 contain RNA from tubers of transformed plants. No ADP-glc1-RNA is detected in positions 93, 89, 62, 52, 53, 23, 61 and 85.

Figure 10:
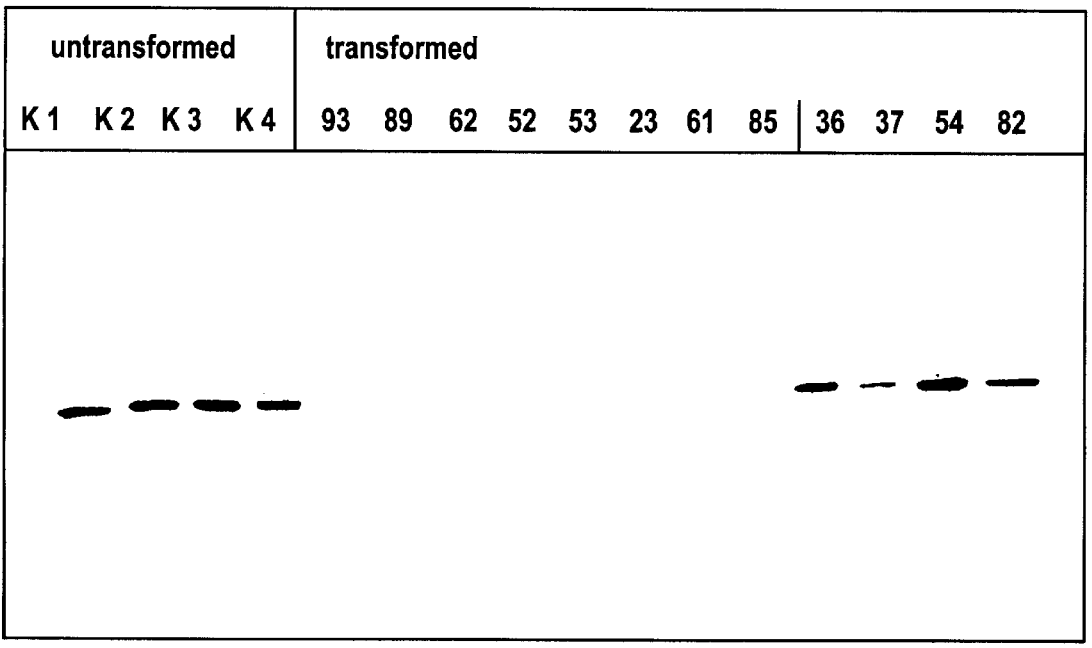

FIG. 10 shows the amount of ADP-glucose pyrophosphorylase I-protein in tubers of untransformed control plants (positions K1-K4) and the reduction in the amount or the disappearance of that protein in tubers of potato plants transformed with the gene 35S-anti-ADP-glc1 (positions 93, 89, 62, 52, 53, 23, 61, 85, 36, 37, 54 and 82).

Markedly less ADP-glucose pyrophosphorylase I protein is present at positions 93, 89, 62, 52, 53, 23, 61 and 85.

DETAILED DESCRIPTION OF THE INVENTION

In order to provide a better understanding of the Examples forming the basis of this invention, all the processes that are necessary for these tests and which are known per se will first of all be listed:

1. Cloning Process

The vectors pUC18/19 and pUC118, and the M13mp10 series (Yanisch-Perron et al., Gene (1985), 33, 103–119) were used for cloning.

For plant transformation, the gene constructions were cloned into the binary vector BIN19 (Bevan, Nucl. Acids Res. (1984), 12, 8711–8720).

2. Bacterial Strains

The *E. coli* strain BMH71-18 (Messing et al., Proc. Natl. Acad. Sci. USA (1977), 24, 6342–6346) or TB1 was used for the pUC and M13mp vectors.

The *E. coli* strain TB1 was used exclusively for the vector BIN19. TB1 is a recombination-negative, tetracycline-resistant derivative of strain JM101 (Yanisch-Perron et al., Gene (1985), 33, 103–119). The genotype of the TB1 strain is (Bart Bartel, personal communication): F' (traD36, proAB, lacI, lacZ M15), (lac, pro), SupE, this, recA, Sr1::Tn10(TCR).

The transformation of the plasmids into the potato plants was carried out by means of the *Agrobacterium tumefaciens* strain LBA4404 (Bevan, M., Nucl. Acids Res. 12, 8711–8721, (1984); BIN19 derivative).

3. Transformation of *Agrobacterium tumefaciens*

In the case of BIN19 derivatives, the insertion of the DNA into the agrobacteria was effected by direct transformation in accordance with the method developed by Holsters et al., (Mol. Gen. Genet. (1978), 163, 181–187). The plasmid DNA of transformed agrobacteria was isolated in accordance with the method developed by Birnboim and Doly (Nucl. Acids Res. (1979), 7, 1513–1523) and was separated by gel electrophoresis after suitable restriction cleavage.

4. Plant Transformation 10 small leaves, damaged with a scalpel, of a sterile potato culture were placed in 10 ml of MS medium with 2% sucrose containing from 30 to 50 μl of an overnight culture *Agrobacterium tumefaciens* grown under selection. After from 3 to 5 minutes of gentle shaking, the Petri dishes were incubated in the dark at 25° C. After 2 days, the leaves were laid out on MS medium with 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% Bacto agar. After incubation for one week at 25° C. and 3000 lux, the claforan concentration in the medium was reduced by half. The subsequent cultivation was effected in accordance with a known method (Rocha-Sosa et al. EMBO J., 8, 29 (1989).

5. Analysis of Genomic DNA from Transgenic Potato Plants

The isolation of genomic plant DNA was effected in accordance with Rogers and Bendich (Plant Mol. Biol. (1985), 5, 69–76.

For the DNA analysis, after suitable restriction cleavage, from 10 to 20 μg of DNA were analysed by means of Southern blotting for the integration of the DNA sequences to be investigated.

6. Analysis of the Total RNA from Transgenic Potato Plants

The isolation of plant total RNA was carried out in accordance with Logemann et al. (Analytical Biochem. (1987), 163, 16–20).

For the analysis, 50 μg portions of total RNA were investigated by means of Northern blotting for the presence of the transcripts sought.

7. Protein Extraction

For the extraction of total protein from plant tissue, pieces of tissue were homogenised in protein extraction buffer (25 mM sodium phosphate pH 7.0, 2 mM sodium hydrogen sulphite), with the addition of 0.1% (w/v) of insoluble polyvinylpyrrolidone (PVP).

After filtration through cellulose, cell detritus was centrifuged off for 20 minutes at 10,000 revolutions per minute and the protein concentration of the supernatant was determined in accordance with the method developed by Bradford (Anal. Biochem. (1976)/72, 248–254).

8. Detection of Foreign Proteins by Means of Immunological Processes (Western Blot)

The protein extracts were separated according to molecular weight by means of gel electrophoresis in SDS-PAGE (sodium dodecylsulphate polyacrylamide) gels. After SDS-PAGE the protein gels were equilibrated for from 15 to 30 minutes in transfer buffer for graphite electrodes (48 g/l of Tris, 39 g/l of glycine, 0.0375 % SDS, 20% methanol) and then transferred in a cooling chamber to a nitrocellulose filter and separated at 1.3 mA/cm² for from 1 to 2 hours. The filter was saturated for 30 minutes with 3% gelatin in TBS buffer (20 mM Tris/HCl pH 7.5, 500 mM NaCl), and the filter was then incubated for 2 hours with the appropriate antiserum in a suitable dilution (1:1000–10000 in TBS buffer) at room temperature. The filter was then washed for 15 minutes each with TBS, TTBS (TBS buffer with 0.1% polyoxyethylene-(20)-sorbitan monolaurate) and TBS buffer. After being washed, the filter was incubated for 1 hour at room temperature with alkaline phosphatase-conjugated goat-anti-rabbit (GAR) antibodies (1:7500 in TBS). The filter was then washed as described above and equilibrated in AP buffer (100 mM tris/HCl pH 9.5, 100 mM NaCl, 5 mM $MgCl_2$). The alkaline phosphatase reaction was started by means of the substrate addition of 70 μl of 4-nitrotetrazolium (NBT) solution (50 mg/ml of NBT in 70% dimethylformamide) and 35 μl of 5-bromo-4-chloro-3-indolyl phosphate (BCIP) (50 mg/ml BCIP in dimethylformamide) in 50 ml of AP buffer. As a rule the first signals were observed after 5 minutes. The reaction can be terminated by transferring the filter into stop solution (20 mM tris/HCl pH 8.0 with 5 mM EDTA). The reaction was carried out in the dark.

9. Esterase Test

The esterase activity of the patatin protein was detected in situ in semi-native SDS polyacrylamide gels (SDS-PAGE) by incubation of the gels in 100 ml of incubation buffer (50 mM Tris/HCl, pH 7.0, 200 mM sodium chloride, 0.1% SDS), to which, as substrates, 500 μl of 1% α-naphthyl acetate solution (1 g of α-naphthyl acetate/100 ml of ethanol) and 5 ml of 2% Fast Blue RR solution were added. As a result of the esterase activity, a brown-black insoluble stain was precipitated which specifically stains the protein bands of native esterase in the gel. The separation of the protein mixture that was not denatured by heating (semi-native) was effected in 12% SDS-PAGE in accordance with Laemmli (1970, Nature, 227, 680–685).

10. Staining of Proteins in Polyacrylamide Gel

After termination of the electrophoresis, the gel was shaken for 2 hours in fixing solution (50% methanol, 10% acetic acid, 40% water), and then left for 4 hours in staining solution (0.05% Coomassie Brilliant Blue R in fixing solution) and subsequently decolored several times in decoloring solution (5% methanol, 7 % acetic acid, 88% water) until clear protein bands appeared.

11. Determination of Glucose, Fructose, Sucrose and Starch a) Extraction

Small portions of tuber (diameter 10 mm) frozen in liquid nitrogen were extracted for 30 minutes at 80° C. in 0.5 ml of buffer (80% (v/v) ethanol; 10 mM HEPES pH 7.5) in a water bath. The supernatant containing the soluble components was poured off and the volume was determined. The supernatant was used to determine soluble sugars.

The insoluble material that remained was rinsed with water and finely ground in a mortar. The extract was then boiled for 1 hour at 95° C. in 0.2 M potassium hydroxide solution, the pH was adjusted to 5.5 with 70 μl of 1N acetic acid and the whole was then centrifuged. Aliquots of the resulting starch solution were used to determine the starch.

b) Quantitative Determination of Soluble Glucose, Fructose and Sucrose

The quantitative determination of soluble glucose, fructose and sucrose was carried out in the following test mixture:

100.0 mM imidazole-HCl, pH 6.9
1.5 mM $MgCl_2$
0.5 mM $NADP^+$
1.3 mM ATP
10–50.0 μl sample
1.0 U glucose 6-phosphate dehydrogenase from yeast.

The mixture was incubated for five minutes. The determination of the sugars was then carried out photometrically by the successive addition of 1.0 U hexokinase from yeast (for the determination of glucose)

1.0 U phosphoglucose isomerase from yeast (for the determination of fructose)

20.0 U invertase from yeast (for the determination of sucrose).

C) Starch Determination

Hydrolytic enzymes were added at 55° C. to the starch solution obtained after the ethanolic extraction under a) and the whole was incubated for twelve hours in the following mixture:

50.0 mM sodium acetate, pH 4.8
1.4 U amyloglucosidase from *Aspergillus niger*
2.0 U α-amylase from porcine pancreas After incubation, the insoluble constituents were removed by 4 minutes of centrifugation at 16,000 g. The resulting glucose in the supernatant was then enzymatically determined as described under b).

12. Determination of ADP-glucose Pyrophosphorylase Activity

The ADP-glucose pyrophosphorylase activity was determined using standard methods (Lin et al., 1988, Plant Physiology 86, 1131–1135).

The following Examples illustrate the preparation of the plasmids according to the invention, the insertion of those plasmids into the plant and the function of the plasmids in those transgenic plants.

EXAMPLE 1

Preparation of the Plasmid P35S-pat and Insertion of the Gene 35S-pat, Located in the Plasmid, into the Plant Genome In order to increase the expression of patatin protein, a plasmid comprising the promoter of 35S RNA of cauliflower mosaic virus (CaMV), which effects a constitutive expression, the polyadenylation signal of the octopine synthase gene of the T-DNA of the Ti-plasmid pTiACH5 and the coding sequence of a patatin gene, present in the form of a genomic clone, was constructed. In the process the coding sequence of the patatin gene was placed between the promoter and the polyadenylation site, the coding strand of the patatin gene being read.

The gene 35S-pat comprises the three fragments A, B and C and was prepared as follows:

Fragment A (529 bp) contains the 35S promoter of cauliflower mosaic virus (CaMV). That fragment includes the nucleotides 6909 to 7437 of CaMV (Franck et al., Cell 21, 285–294) and is located between the Eco RI/Kpn I cleavage site. Fragment B (191 bp) contains the polyadenylation signal of gene 3 of the T-DNA of the Ti-plasmid pTiACH5 (Gielen et al., EMBO J., 3, 835–846), nucleotides 11749–11939, which was isolated as a Pvu II fragment from the plasmid pAGV 40 (Herrera-Estrella et al., (1983) Nature 303, 209–213) and, after the addition of Sph I linkers to the Pvu II cleavage site, was cloned between the Sph I/Hind III cleavage sites of the polylinker of pUC18.

Fragments A and B were joined by a partial pUC18 polylinker (Kpn I to Sph I) and cloned in the form of an expression cassette into the Eco RI and Hind III cleavage sites of the binary vector BIN19 (M. Bevan, 1984, Nucl. Acids Res., 12, 8711–8721). Fragment C includes a 6.0 kb fragment of the genomic patatin clone B33 (M. Rocha-Sosa et al., 1989, EMBO J., 8, 23–29). After partial Dra I digestion, the Dra I/Eco RI fragment (cleavage site of Dra I at position −27 of the patatin clone B33, single Eco RI cleavage site in the genomic clone B33) was provided with blunt ends by means of Klenow polymerase and cloned into the Sma I cleavage site of the polylinker positioned between fragments A and B.

Figure 1:
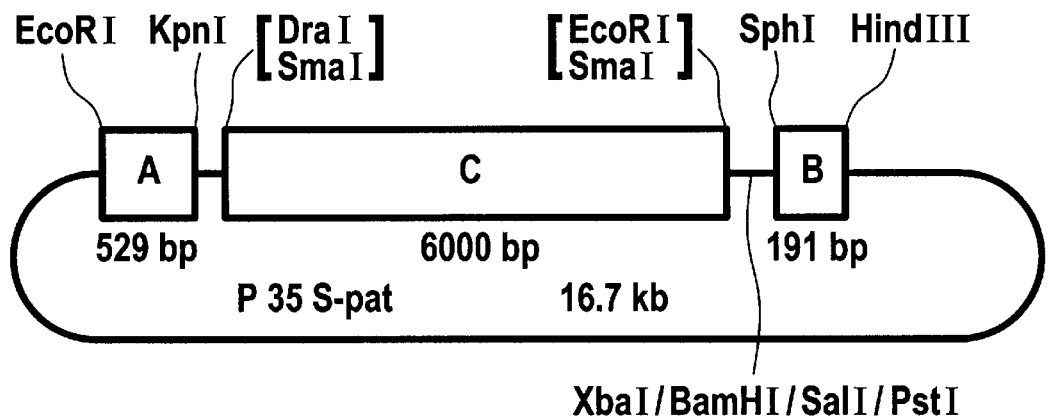
FIG. 1 shows the structure of the 16.7 kb plasmid p35S-pat. The gene 35S-pat located in the plasmid contains the following fragments:
 A=Fragment A (529 bp) contains the 35S promoter of cauliflower mosaic virus (CaMV). That fragment includes the nucleotides 6909 to 7437 of CaMV.
 B=Fragment B (191 bp) contains the polyadenylation signal of gene 3 of the T-DNA of the Ti-plasmid pTiACH5. That fragment includes the nucleotides 11749–11939.
 C=Fragment C (6000 bp) includes the fragment of the genomic patatin clone B33.

The plasmid p35S-pat has a size of 16.7 kb (see FIG. 1). The gene 35S-pat located in the plasmid p35S-pat was inserted into binary vectors and, by means of the agrobacteria system described above, was inserted into potato plants. Intact and fertile plants were regenerated from transformed cells.

In order to investigate the tubers of regenerated transgenic plants for patatin protein, 50 μg of an undenatured tuber protein extract prepared as described under point 7 on page 16 were separated on a 12% SDS-PAGE gel and stained in situ with α-naphthyl acetate and Fast Blue RR in order to detect esterase activity. This analysis showed that the transformation leads to the occurrence of new patatin-coded esterase activity in plants H7-(35S-33) 5 to 11.

Controls C1 and C2, which are extract samples from tubers of untransformed Désirée plants, and the tuber extracts from plants H7-(35S-33) 8 and 11, which are control transformations with a different plasmid, exhibited no new esterase activity (see FIG. 6).

It can therefore be shown that the protein content in the potato tuber can be increased by the insertion and expression of the gene 35S-pat located in the plasmid p35S-pat.

EXAMPLE 2
Preparation of the Plasmid P35S-anti-pat and Insertion of the Gene 35S-anti-pat, Located in the Plasmid, into the Plant Genome The 40 kDa patatin protein makes up from 20 to 40% of the total protein. A reduction in the amount of protein in the liquid produced during processing is desirable. In order to reduce the expression of the patatin protein, a plasmid comprising the promoter of the 35S RNA of cauliflower mosaic virus (CaMv), which effects a constitutive expression, the polyadenylation signal of the octopine synthase gene of the T-DNA of the Ti-plasmid pTiACH5 and the coding sequence of a patatin gene, present in the form of a cDNA clone, was constructed. In the process the coding sequence of the patatin cDNA was placed between the promoter and the polyadenylation site in such a manner that the 3'-end of the coding sequence is directly adjacent to the promoter, while the 5'-end of the coding sequence is directly adjacent to the polyadenylation site. The normal arrangement of the coding sequence relative to the promoter and the polyadenylation signal is thus inverted, which in transgenic potato plants leads to the formation of an RNA that is "anti-sense" with respect to the "sense" patatin RNA normally formed in the tuber. The presence of an "anti-sense" RNA leads to a quantitative reduction in the patatin sense RNA and thus to a reduction in patatin protein.

The gene 35S-anti-pat comprises the three fragments A, B and C and was prepared as follows:

Fragment A (529 bp) contains the 35S promoter of cauliflower mosaic virus (CaMV). That fragment includes the nucleotides 6909 to 7437 of CaMV (Franck et al., Cell 21, 285–294) and is located between the Eco RI/Kpn I cleavage site. Fragment B (191 bp) contains the polyadenylation signal of gene 3 of the T-DNA of the Ti-plasmid pTiACH5 (Gielen et al., EMBO J., 3, 835–846), nucleotides 11749–11939, which was isolated as a Pvu II fragment from the plasmid pAGV 40 (Herrera-Estrella et al., (1983) Nature 303, 209–213) and, after the addition of Sph I linkers to the Pvu II cleavage site, was cloned between the Sph I/Hind III cleavage sites of the polylinker of pUC18.

Fragments A and B were joined by a partial pUC18 polylinker (Kpn I to Sph I) and cloned in the form of an expression cassette into the Eco RI and Hind III cleavage sites of the binary vector BIN19 (M. Bevan, 1984, Nucl. Acids Res., 12, 8711–8721). Fragment C was obtained by cloning the Pst I fragment of the cDNA clone pcT 58 (Rosahl et al., 1986, Mol. Gen. Genetics 203, 214–220) into the Pst I cleavage site of the vector M13mp10. A 1.25 kb Sal I/Sma I fragment was then isolated from that vector, the Sal I cleavage site being located in the polylinker of the vector M13mp10, and the Sma I cleavage site being located in the cDNA insert (compare the sequence of the clone pcT 58 in R. Schmidt, Diplomarbeit (thesis), University of Cologne, 1985). The fragment was ligated specifically into the Sma I and Sal I cleavage sites of the polylinker located between fragments A and B. The plasmid p35s-anti-pat has a size of 12.0 kb (see FIG. 2).

The gene 35S-anti-pat located in the plasmid p35S-anti-pat was inserted into binary vectors and, by means of the agrobacteria system described above, inserted into potato plants. Intact and fertile plants were regenerated from transformed cells.

In order to detect patatin RNA and patatin protein in plants that contained the gene 35S-anti-pat, a Northern blot analysis of transgenic patatin anti-sense plants (Pas 58) was carried out. For that purpose 50 μg of total RNA from tubers was separated in a 1.5% formaldehyde/agarose gel and transferred to a nylon filter (Hybond N., Amersham). The filter was hybridised with a radioactively labelled patatin fragment (pcT 58 (Rosahl et al., Mol. Gen. Genetics 203, 214–220 (1986)). The signals were rendered visible by means of autoradiography. The bands (marked with an arrow) indicate specifically the presence of patatin RNA, and the blackness of the bands is a measure of the concentration of the particular RNA concerned (see FIG. 7). Analysis of the tubers of regenerated transgenic plants for the presence of patatin RNA and patatin protein showed a drastic reduction in the patatin RNA in 12 of 16 cases tested (16 independently transformed plants). In some cases no patatin RNA was detected at all. FIG. 7 shows 13 of 16 samples from transformed plants.

In addition, after separation by means of gel electrophoresis, protein extracts isolated from tubers were investigated in respect of patatin protein content by means of Coomassie Blue staining. For that purpose 25 μg of denaturated protein each were taken from an untransformed potato tuber of the Désirée variety and a transgenic plant transformed with the gene 35S-anti-pat, applied to a 12% SDS-PAGE gel and separated. The protein bands were then stained with Coomassie Blue, the protein bands separated in the gel becoming visible. The intensity of the colour was a measure of the concentration (see FIG. 8, intensity of the blackness). In all transgenic plants transformed with the gene 35S-anti-pat that contained a greatly reduced amount of patatin RNA, a significant reduction in the patatin protein to approximately 10% of the amount contained in a genetically unmodified plant was also detected (see FIG. 8). It was therefore possible to show that the protein content in the potato tuber is greatly reduced by the insertion and expression of the gene 35S-anti-pat.

The concentrations of other proteins, for example a proteinase inhibitor, were not affected. This can be demonstrated by means of densitometry curves of the two protein tracks (see FIG. 8).

EXAMPLE 3
Preparation of the Plasmid P35S-anti-ADP-glc1 and Insertion of the Gene 35S-anti-ADP-glc1, Located in the Plasmid, into the Plant Genome Using a heterologous sample of maize, various clones that cross-hybridise with that sample were identified from a cDNA bank set up using the expression vector xgt11. Those clones were sub-cloned from the vector xgt11 into the vector pUC18. The determination of the nucleotide sequence clearly identified those clones that are cDNA clones coding for one of the two isoforms (isoform I) of the potato ADP-glucose pyrophosphorylase.

That cDNA was provided with the promoter of the 35S-RNA of cauliflower mosaic virus and the polyadenylation signal of octopine synthase of the Ti-plasmid pTiACH5. In the process the orientation of the segment coding for the cDNA of ADP-glucose pyrophosphorylase was selected so that the non-coding strand of the cDNA is read.

The gene 35S-anti-ADP-glc1 comprises the three fragments A, B and C and was prepared as follows:

Fragment A (529 bp) contains the 35S promoter of cauliflower mosaic virus (CaMV). That fragment includes the nucleotides 6909 to 7437 of CaMV (Franck et al., Cell 21, 285–294) and is located between the Eco RI/Kpn I cleavage site. Fragment B (191 bp) contains the polyadenylation signal of gene 3 of the T-DNA of the Ti-plasmid pTiACH5 (Gielen et al., EMBO J., 3, 835–846), nucleotides 11749–11939, which was isolated as a Pvu II fragment from the plasmid pAGV 40 (Herrera-Estrella et al., (1983) Nature 303, 209–213) and, after the addition of Sph I linkers to the Pvu II cleavage site, was cloned between the Sph I/Hind III cleavage sites of the polylinker of pUC18.

Fragment C contains a 1589 nucleotide Eco RI fragment that codes for isoform I of the two isoforms of the potato ADP-glucose pyrophosphorylase. The sequence of the 1589 nucleotides of that clone is shown in Müller-Röber et al., Mol. Gen. Genetics 224, 136–146 (1990) as a sequence of the clone B22-1. The orientation of that cDNA clone is so selected that the non-coding strand is read (see Example 2), which in a transgenic potato plant leads to the formation of a so-called "anti-sense" RNA. The presence of the anti-sense RNA leads to a reduction in the "sense"-ADP-glucose pyrophosphorylase I RNA formed in the potato and hence to a reduction in the biosynthesis of starch. The gene 35S-anti-ADP-glc1 is in the form of an Eco RI/Hind III fragment in the polylinker of the vector pUC18.

The plasmid p35S-anti-ADP-glc1 has a size of 5.0 kb (see FIG. 3).

The gene 35S-anti-ADP-glc1, located in the plasmid p35S-anti-ADP-glc1, was inserted into binary vectors and, by means of the agrobacteria system described above, transferred into potato plants. Intact and fertile plants were regenerated from transformed cells. The tubers of those plants were investigated for the presence of ADP-glucose pyrophosphorylase glc1 RNA by means of Northern blot analysis (see point 6, page 16). In some plants that have been transformed with the gene 35S-anti-ADP-glc1, no endogenous cellular RNA of that gene can be detected (see FIG. 9). Likewise, no protein can be detected by means of Western blotting (see FIG. 10). The associated reduction in starch concentration and ADP-glucose pyrophosphorylase activity is determined enzymatically using standard methods (Plaxton, W. L. and Preiss, J. (1987) Plant Physiology 83, 105–112, Lin et al. (1988) Plant Physiology 86, 1131–1135).

The ADP-glucose pyrophosphorylase activity measured in tuber extracts of untransformed and transgenic (35S-anti-ADP-glc1) potato plants is as follows:

| Plant | ADP-glucose pyrophosphorylase activity (%) |
| --- | --- |
| K 1 | 101.5 |
| K 2 | 92.0 |
| K 3 | 97.2 |
| K 4 | 109.3 |
| T 89 | 1.5 |
| T 93 | 2.1 |
| T 62 | 3.1 |
| T 52 | 3.2 |
| T 53 | 4.4 |
| T 23 | 5.2 |
| T 61 | 8.1 |
| T 85 | 17.2 |
| T 36 | 92.6 |
| T 37 | 56.4 |
| T 54 | 110.2 |
| T 82 | 82.4 |

The percentage relates to the activity measured in untransformed plants, the 100% value corresponding to the mean value of the activity measured in the untransformed plants.

The starch content in tubers of untransformed and transgenic (35S-anti-ADP-glc1) potato plants is as follows:

| Plant | Starch content (%) |
| --- | --- |
| K 1 | 87.2 |
| K 2 | 100.9 |
| K 3 | 103.4 |
| K 4 | 108.5 |
| T 89 | 1.8 |
| T 93 | 1.4 |
| T 62 | 3.9 |
| T 52 | 7.0 |
| T 53 | 7.2 |
| T 23 | 8.9 |
| T 61 | 24.4 |
| T 85 | 29.0 |
| T 36 | 90.6 |
| T 37 | 75.6 |
| T 54 | 96.1 |
| T 82 | 89.4 |

The percentage relates to the starch content measured in untransformed plants, the 100% value corresponding to the mean value of the contents measured in the untransformed plants.

The sucrose content in tubers of untransformed and transgenic (35S-anti-ADP-glc1) potato plants is as follows:

| Plant | Sucrose content (%) |
| --- | --- |
| K 1 | 1.8 |
| K 2 | 1.8 |
| K 3 | 2.2 |
| K 4 | 2.6 |
| T 89 | 31.0 |
| T 93 | 31.6 |
| T 62 | 27.8 |
| T 52 | 21.5 |
| T 53 | 24.9 |
| T 23 | 20.5 |
| T 61 | 17.5 |
| T 85 | 10.9 |
| T 36 | 2.4 |
| T 37 | 4.6 |

-continued

| Plant | Sucrose content (%) |
|---|---|
| T 54 | 2.6 |
| T 82 | 2.6 |

The percentage represents the sucrose content measured in the tubers, based on the dry weight. K represents untransformed plants, T represents transgenic plants.

It can be seen from those results that the insertion of the gene 35S-anti-ADP-glc1, located in the plasmid p35S-anti-ADP-glc1, into the plant has led to a drastic reduction in ADP-glucose pyrophosphorylase activity by a factor of up to 50 in comparison with untransformed control plants. In the tubers of those transgenic potato plants that exhibit a great reduction in ADP-glucose pyrophosphorylase activity, a further consequence that is observed is a drastic reduction in the amount of starch contained therein in comparison with the amount contained in untransformed control plants. A further surprising finding is that the tubers in which the starch content is drastically reduced contain high concentrations of disaccharides. Those concentrations are mainly sucrose, which makes up to 30% of the dry mass of the tubers. That means that, as a result of the transfer of the gene 35S-anti-ADP-glc1 located in the plasmid p35S-anti-ADP-glc1, the potato tuber stores, instead of starch, large amounts of disaccharides. From a plant that stores starch, a plant that stores sugar has thus been produced.

In addition, by means of the insertion of the gene 35S-anti-ADP-glc1, located in the plasmid p35S-anti-ADP-glc1, into transgenic plants the starch biosynthesis of which has been inhibited, a considerably greater number of tubers (approximately 4 to 5 times as many) are obtained than in the case of control plants.

EXAMPLE 4
Preparation of the Plasmid P35S-anti-ADP-glc2 and Insertion of the Gene 35S-anti-ADP-glc2. Located in the Plasmid, into the Plant Genome Using a heterologous sample of maize, various clones that cross-hybridise with that sample were identified from a cDNA bank set up in the expression vector gt11. Those clones were sub-cloned from the vector gt11 into the vector pUC18. Determination of the nucleotide sequence clearly identified those clones that are cDNA clones coding for isoform II of the potato ADP-glucose pyrophosphorylase.

That cDNA was provided with the promoter of the 35S RNA of cauliflower mosaic virus and the polyadenylation signal of octopine synthase of the Ti-plasmid pTiACH5. In the process the orientation of the segment coding for the cDNA of ADP-glucose pyrophosphorylase was so selected that the non-coding strand of the cDNA is read.

The gene 35S-anti-ADP-glc2 comprises the three fragments A, B and C and was prepared as follows:

Fragment A (529 bp) contains the 35S promoter of cauliflower mosaic virus (CaMV). That fragment includes the nucleotides 6909 to 7437 of CaMV (Franck et al., Cell 21, 285–294) and is located between the Eco RI/Kpn I cleavage site. Fragment B (191 bp) contains the polyadenylation signal of gene 3 of the T-DNA of the Ti-plasmid pTiACH5 (Gielen et al., EMBO J., 3, 835–846), nucleotides 11749–11939, which was isolated as a Pvu II fragment from the plasmid pAGV 40 (Herrera-Estrella et al., (1983) Nature 303, 209–213) and, after the addition of Sph I linkers to the Pvu II cleavage site, was cloned between the Sph I/Hind III cleavage sites of the polylinker of pUC18.

Fragment C contains a 1.7 kb Eco RI fragment that codes for isoform II of the two isoforms of the potato ADP-glucose pyrophosphorylase. The orientation of that cDNA clone was so selected that the non-coding strand is read (see Example 2), which in the transgenic potato plant leads to the formation of a so-called "anti-sense" RNA. The presence of the anti-sense RNA leads to a reduction in the sense-ADP-glucose pyrophosphorylase 2 RNA formed in the potato and hence to an inhibition of the biosynthesis of starch. The gene 35S-anti-ADP-glc2 is in the form of an Eco RI/Hind III fragment in the polylinker of the vector pUC18 (see FIG. 4).

The gene 35S-anti-ADP-glc2 located in the plasmid p35S-anti-ADP-glc2 was inserted into binary vectors and, by means of the agrobacteria system described above, transferred into potato plants. Intact and fertile plants were regenerated from transformed cells. Those plants were investigated for the presence of ADP-glucose pyrophosphorylase-glc2 RNA by means of Northern blot analysis. Plants that have been transformed with the gene 35S-anti-ADP-glc2 located in the plasmid p35S-anti-ADP-glc2 exhibit a reduced amount of the endogenous cellular RNA of that gene. The associated reduction in the amount of starch and in ADP-glucose pyrophosphorylase activity is determined enzymatically using standard methods (see Example 3).

EXAMPLE 5
Preparation of the Plasmid P35S-anti-ADP-glc1+2 and Insertion of the Gene 35S-anti-ADP-glc1+2, Located in the Plasmid, into the Plant Genome The gene 35S-anti-ADP-glc1+2 was prepared by insertion of the 1.5 kb Xba I fragment from the plasmid p35S-anti-ADP-glc1 into the Xba I site of the plasmid p35S-ADP-glc2. In the process, the orientation of the Xba I fragment was so selected that the non-coding strand of the Xba I fragment is read, which thus leads in the transgenic potato plant to the formation of a so-called "anti-sense" RNA of the two isoforms (isoform I and II) of the potato ADP-glucose pyrophosphorylase. The presence of the "anti-sense" RNAs leads to a reduction in the sense-ADP-glucose pyrophosphorylase 1 and the sense-ADP-glucose pyrophosphorylase 2 RNAs formed in the potato and hence to a reduction in the biosynthesis of starch. The gene 35S-anti-ADP-glc1+2 is in the form of an Eco RI/Hind III fragment in the polylinker of the vector pUC18 (see FIG. 5).

The gene 35S-anti-ADP-glc1+2 located in the plasmid p35S-anti-ADP-glc1+2 comprises the four fragments A, B C1 and C2 and was prepared as follows:

Fragment A (529 bp) contains the 35S promoter of cauliflower mosaic virus (CaMV). That fragment includes the nucleotides 6909 to 7437 of CaMV (Franck et al., Cell 21, 285–294) and is located between the Eco RI/Kpn I cleavage site. Fragment B (191 bp) contains the polyadenylation signal of gene 3 of the T-DNA of the Ti-plasmid pTiACH5 (Gielen et al., EMBO J., 3, 835–846), nucleotides 11749–11939, which was isolated as a Pvu II fragment from the plasmid pAGV 40 (Herrera-Estrella et al., (1983) Nature 303, 209–213) and, after the addition of Sph I linkers to the Pvu II cleavage site, was cloned between the Sph I/Hind III cleavage sites of the polylinker of pUC18.

Fragment C1 contains a 1.7 kb Eco RI fragment that codes for isoform II of the two isoforms of the potato ADP-glucose pyrophosphorylase. The orientation of that cDNA clone is so selected that the non-coding strand is read (see Example 2) which in the transgenic potato plant leads to the formation of a so-called "anti-sense" RNA.

Fragment C2 contains the 1.5 kb Xba I/Xba I fragment of p35S-anti-ADP-glc1 that codes for isoform I of the two ADP-glucose pyrophosphorylases.

The orientation of fragments C1 and C2 was so selected that the non-coding strand of each fragment C1 and C2 is read, which in the transgenic potato plant leads to the formation of a so-called "anti-sense" RNA of the two isoforms (isoform I and isoform II) of the potato ADP-glucose pyrophosphorylase.

The gene 35S-anti-ADP-glc1+2 is in the form of an Eco RI/Hind III fragment in the polylinker of the vector pUC18.

The gene 35S-anti-ADP-glc1+2 contained in the plasmid p35S-anti-ADP-glc1+2 was inserted into binary vectors and, by means of the agrobacteria system, transferred into potato plants. Intact and fertile plants were regenerated from transformed cells. Those plants were investigated for the presence of ADP-glucose pyrophosphorylase I RNA and ADP-glucose pyrophosphorylase II RNA by means of Northern blot analysis (see point 6 on page 16). Plants that have been transformed with the gene 35S-anti-ADP-glc1+2 located in the plasmid p35S-anti-ADP-glc1+2 exhibit a greatly reduced amount of the endogenous cellular RNAs of the two ADP-glucose pyrophosphorylases (I and II). The associated reduction in starch concentration and in ADP-glucose pyrophosphorylase activity was determined enzymatically using standard methods (see Example 3).

We claim:

1. A plasmid comprising at least one DNA sequence encoding ADP-glucose pyrophosphorylase derived from potato in anti-sense orientation, which when used to produce a transgenic plant leads to a reduction in starch concentration and an increase in the concentration of at least sucrose, said DNA sequence being operably linked to at least one plant regulatory sequence, said plant regulatory sequence being capable of regulating the expression of said DNA sequence in anti-sense orientation of said transgenic plant.

2. A plasmid as claimed in claim 1, wherein the DNA sequence codes for at least one isoform of the ADP-glucose pyrophosphorylase of potato selected from the group consisting of isoform I and isoform II.

3. A plasmid as claimed in claim 1, wherein the DNA sequence in anti-sense orientation is operably linked to a plant promoter and is operably linked to a plant termination signal.

4. A plasmid which comprises at least one gene construct selected from the group consisting of 35S-anti-ADP-glc1, 35S-anti-ADP-glc2 and 35S-anti-ADP-glc1+2.

5. A plasmid as claimed in claim 4, wherein the plasmid is p35S-anti-ADP-glc1 (DSM 5879).

6. A plasmid as claimed in claim 4, wherein the plasmid is p35S-anti-ADP-glc2 (DSM 5880).

7. A plasmid as claimed in claim 4, wherein the plasmid is p35S-anti-ADP-glc1+2 (DSM 5881).

8. A cell of a starch producing plant comprising an expressible, anti-sense DNA sequence encoding ADP-glucose pyrophosphorylase derived from potato, said anti-sense DNA sequence leading to a reduction in starch concentration and an increase in concentration of at least sucrose in seeds or tubers when expressed as anti-sense RNA.

9. A cell of a starch producing plant that comprises a DNA sequence derived from a starch producing plant that leads to both reduction in the concentration of starch and an increase in the concentration of at least sucrose in seeds and tubers, wherein said DNA sequence is a gene construct selected from the group consisting of 35S-anti-ADP-glc1, 35S-anti-ADP-glc2 and 35S-anti-ADP-glc1+2.

10. A cell as claimed in claim 9, wherein said gene construct is present on a plasmid selected from the group consisting of p35S-anti-ADP-glc1 (DSM 5879), p35S-anti-ADP-glc2 (DSM 5880) and p35S-anti-ADP-glc1+2 (DSM 5881).

11. A plant produced from a cell derived from a starch producing plant, said plant cell comprising at least one expressible DNA sequence derived from potato encoding ADP-glucose pyrophosphorylase in an anti-sense orientation, that leads to a reduction in starch concentration and an increase in concentration of at least sucrose in seeds or tubers of said plant when expressed as anti-sense RNA.

12. A plant as claimed in claim 11, which comprises at least one gene construct selected from the group consisting of 35S-anti-pat, 35S-anti-ADP-glc1, 35S-anti-ADP-glc2 and 35S-anti-ADP-glc1+2.

13. A plant as claimed in claim 11, wherein said DNA sequence is a gene construct selected from the group consisting of 35S-anti-ADP-glc1, 35S-anti-ADP-glc2 and 35S-anti-ADP-glc1+2.

14. A plant as claimed in claim 13, wherein said gene construct is present on a plasmid selected from the group consisting of p35S-anti-ADP-glc1 (DSM 5879), p35S-anti-ADP-glc2 (DSM 5880) and p35S-anti-ADP-glc1+2 (DSM 5881).

15. A method of producing saccharides comprising the steps of:
   a) collecting potato tubers which express an anti-sense sequence of at least one isoform of potato ADP-glucose pyrophosphorylase: and
   b) extracting saccharides from the potato tubers collected in step (a).

16. A method of producing a transgenic starch producing plant comprising the steps of:
   a) transforming at least one plant cell of a starch producing plant with a plasmid p35S-anti-pat (DSM 5878) and with at least one plasmid selected from the group consisting of p35S-anti-ADP-glc1 (DSM 5879), p35S-anti-ADP-glc2 (DSM 5880) and p35S-anti-ADP-glc1+2 (DSM 5881); and
   b) producing a transgenic starch producing plant from the plant cell of step (a).

17. A cell of a starch producing plant containing a plasmid p35S-anti-pat (DSM 5878) and at least one plasmid selected from the group consisting of p35S-anti-ADP-glc1 (DSM 5879), p35S-anti-ADP-glc2 (DSM 5880) and p35S-anti-ADP-glc1+2 (DSM 5881).

18. A transgenic starch producing plant produced by the method as claimed in claim 16.

19. Potato tubers that comprise both a DNA sequence derived from a starch producing plant that codes for at least one subunit of an ADP-glucose phosphorylase protein and a DNA sequence that codes for patatin protein, both in anti-sense orientation.

20. A method of producing saccharides as claimed in claim 15, wherein the potato tubers also express an anti-sense patatin RNA sequence.

21. A potato cell comprising an expressible, anti-sense DNA sequence derived from a potato plant encoding ADP-glucose pyrophosphorylase, said anti-sense DNA sequence leading to a reduction in starch concentration and an increase in concentration of at least sucrose when expressed as anti-sense RNA.

22. A potato plant produced from a potato cell, said potato cell comprising at least one expressible DNA sequence derived from a potato plant encoding ADP-glucose pyrophosphorylase in an anti-sense orientation, that leads to a reduction in starch concentration and an increase in concentration of at least sucrose of said potato plant when expressed as anti-sense RNA.

23. A method of producing a transgenic starch producing plant cell comprising stably incorporating into the genome of a recipient plant cell at least one donor DNA sequence derived from potato encoding a polypeptide selected from the group consisting of ADP-glucose pyrophosphorylase isoform I and II.

24. A method of producing a transgenic starch producing plant comprising stably incorporating into the genome of a recipient plant cell at least one donor DNA sequence derived from potato encoding a polypeptide selected from the group consisting of ADP-glucose pyrophosphorylase isoform I and II, and regenerating a whole plant from said transformed recipient plant cell.

25. A plant cell obtainable according to the method of claim 23.

26. A plant obtainable according to the method of claim 24.

* * * * *